(12) United States Patent
Kim et al.

(10) Patent No.: US 10,081,882 B2
(45) Date of Patent: Sep. 25, 2018

(54) PORTABLE APPARATUS FOR SURFACE INSPECTION AND ELECTROLYTIC POLISHING

(71) Applicant: Frontics, Inc., Seoul (KR)

(72) Inventors: Gwang Ho Kim, Gyeonggi-Do (KR); Heui Gwang Jang, Seoul (KR)

(73) Assignee: Frontics, Inc., Seoul (KR)

( * ) Notice: Subject to any disclaimer, the term of this patent is extended or adjusted under 35 U.S.C. 154(b) by 392 days.

(21) Appl. No.: 14/921,289

(22) Filed: Oct. 23, 2015

(65) Prior Publication Data

US 2016/0145763 A1 May 26, 2016

(30) Foreign Application Priority Data

Nov. 26, 2014 (KR) .......................... 10-2014-0166293

(51) Int. Cl.
  *C25F 7/00* (2006.01)
  *C25F 3/16* (2006.01)
  *G01N 21/88* (2006.01)

(52) U.S. Cl.
  CPC .................. *C25F 7/00* (2013.01); *C25F 3/16* (2013.01); *G01N 21/88* (2013.01); *G01N 2201/062* (2013.01)

(58) Field of Classification Search
  None
  See application file for complete search history.

(56) References Cited

U.S. PATENT DOCUMENTS

| 2,967,813 | A | * | 1/1961 | Lindsay | C25F 3/14 204/224 R |
| 4,883,576 | A | * | 11/1989 | Gemma | B62D 57/00 180/168 |
| 5,135,632 | A | * | 8/1992 | Weber | C25F 7/00 204/224 M |
| 2004/0003894 | A1 | * | 1/2004 | Hsu | C25D 5/22 156/345.12 |
| 2007/0205112 | A1 | * | 9/2007 | Kodera | B23H 5/08 205/641 |
| 2008/0121529 | A1 | * | 5/2008 | Tohma | C25F 3/02 205/640 |
| 2017/0276624 | A1 | * | 9/2017 | Chen | G01N 27/07 |

FOREIGN PATENT DOCUMENTS

GB 750123 * 6/1956 .............. C25F 7/00

* cited by examiner

*Primary Examiner* — Stefanie S Wittenberg
(74) *Attorney, Agent, or Firm* — Mintz Levin Cohn Ferris Glovsky and Popeo, P.C.; Kongsik Kim; Derek E. Constantine

(57) ABSTRACT

Provided herein is a portable apparatus for surface inspection and electrolytic polishing, the apparatus including a housing where a motor and controller are embedded. The apparatus also includes a screw axis rotatable by the motor and a cylinder with a ball nut coupled to the screw axis and coupled to a slider. A plurality of guide members are included that each have an upper end coupled to the housing and a lower end coupled to a base plate. The guide member penetrates the slider, and the slider moves up and down along the guide members with the cylinder. A surface inspector and an electrolytic polisher are coupled to the slider and move up and down together with the slider allowing the surface inspector and the electrolytic polisher to test a test subject in various industrial fields, such as machinery, construction, chemicals, and the like.

12 Claims, 5 Drawing Sheets

PORTABLE APPARATUS FOR SURFACE INSPECTION AND ELECTROLYTIC POLISHING

CROSS-REFERENCE TO RELATED APPLICATION

The present application claims priority to Korean patent application number 10-2014-0166293, filed on Nov. 26, 2014, the entire disclosure of which is incorporated herein in its entirety by reference.

TECHNICAL FIELD

Various embodiments of the present invention relate to a portable apparatus for surface inspection and electrolytic polishing, and more particularly, to a portable apparatus for surface inspection and electrolytic polishing capable of testing a surface inspector and electrolytic polisher on a test subject in various industrial fields of machinery, construction, and chemicals regardless of the type of the testing place, thereby reducing the cost and process of the test, and saving the manpower and time necessary for installing an apparatus for surface inspection and apparatus for electrolytic polishing.

BACKGROUND ART

A surface inspector is configured to inspect the surface structure of a test subject, that is, to photograph an etched surface illumination state of the test subject, a fine circuitry state of an IC chip and the like, and/or a foreign substance attachment state of a semiconductor surface and the like with an imaging device such as a micro digital camera, and to transmit the photographed result.

Furthermore, an electrolytic polisher is configured to electrolyze the surface of a processing subject to polish the surface by applying a voltage between an anode and cathode, where the processing subject is made of a metal that can be dissolved in the electrolytic solution as the anode, and where the processing metal that cannot be dissolved in the electrolytic solution is the cathode.

A surface inspector and electrolytic polisher can be large and heavy, and thus the surface inspector and electrolytic polisher can have to be fixedly installed inside a testing room to be used. Furthermore, a test subject often has to be moved to a testing room and fixed to a test apparatus to be tested.

In order to perform both the surface inspection and the electrolytic polishing, the test subject has to be moved from one apparatus to another, which is inconvenient.

Furthermore, various components and structures that are installed in a variety of industrial fields, such as machinery, construction, and chemicals, not only are large and heavy, but also their properties may have changed in the process of being installed on site, or they may have been installed after their shapes or structures have already been changed. So when the final safety of an installed component or structure is checked, a component or structure must be tested while in its installed state, which can lead to problems.

In order to perform both surface inspection and electrolytic polishing in the industrial fields of machinery, construction, chemicals and the like, both a surface inspector and an electrolytic polisher have to be installed, causing problems by requiring increased operating process, manpower and time.

SUMMARY

A purpose of the present disclosure is to resolve the aforementioned. Provided herein is a portable apparatus for surface inspection and electrolytic polishing capable of testing a surface inspector and electrolytic polisher on a test subject in various industrial fields, such as machinery, construction, and chemicals, regardless of the testing place, thereby reducing the cost and the process.

Another purpose of the present disclosure is to provide a portable apparatus for surface inspection and electrolytic polishing that saves effort and time that are required for installing both a surface inspector and an electrolytic polisher regardless of the testing place.

However, the present disclosure is in no way limited to the aforementioned purposes, and further purposes not explicitly stated herein will be clearly understandable to those skilled in the art based on the following description.

According to an embodiment of the present disclosure, a portable apparatus for surface inspection and electrolytic polishing is provided. The apparatus can include a housing, a screw axis, a cylinder, a plurality of guide members, and a surface inspector and an electrolytic polisher. The housing can have a motor and controller embedded therein. The screw axis can be configured to be rotated by the motor. The cylinder can be configured to accommodate a ball nut coupled to the screw axis, and can be configured to be coupled to a slider. Each of the plurality of guide members can have an upper end coupled to the housing and a lower end coupled to a base plate and therefore fixed. The apparatus can also include the slider through which the guide members penetrate and therefore couple thereto, and the slider can be configured to move up and down along the guide members together with the cylinder during operation of the motor. The surface inspector and electrolytic polisher can be coupled to the slider and can be configured to move up and down together with the slider.

According to the aforementioned embodiments of the present disclosure, it is possible to test a surface inspector and an electrolytic polisher on a test subject in various industrial fields, such as machinery, construction, and chemicals, regardless of the testing place, thereby providing an effective way of reducing the cost and the process.

Furthermore, according to the aforementioned embodiments of the present disclosure, effort and time necessary for installing a surface inspector and an electrolytic polisher are also reduced.

BRIEF DESCRIPTION OF THE DRAWINGS

The above and other features and advantages of the present invention will become more apparent to those of ordinary skill in the art by describing in detail embodiments with reference to the attached drawings in which.

DETAILED DESCRIPTION

Figure 1:
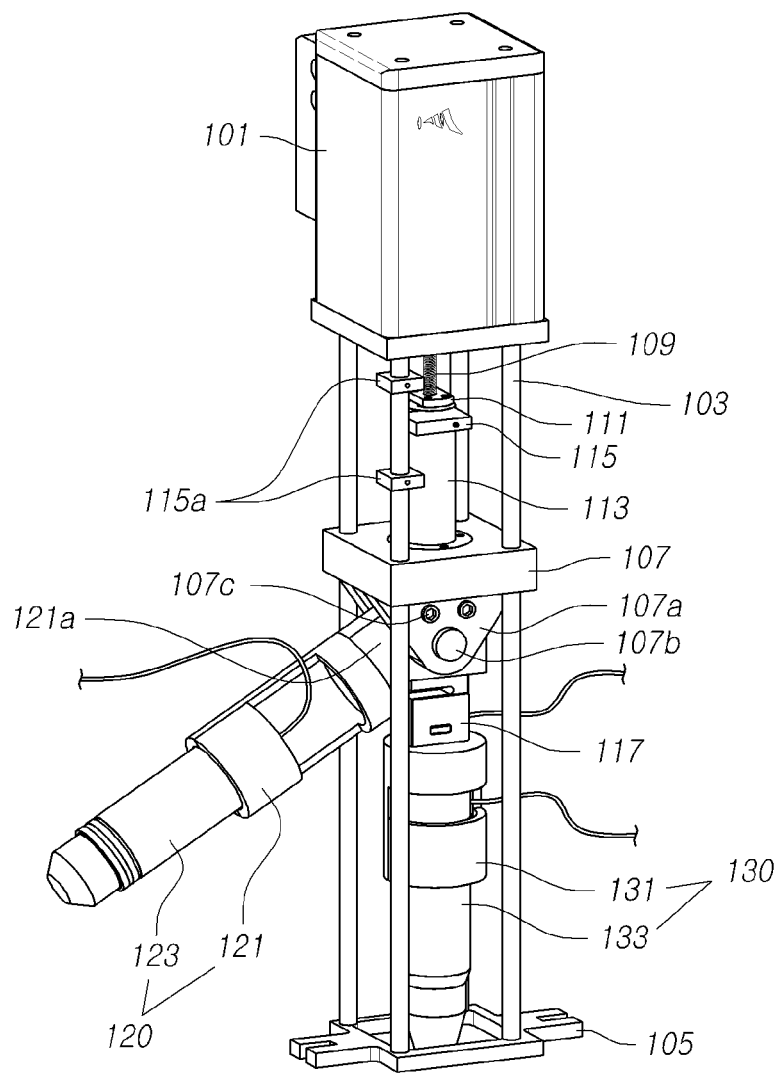
FIG. 1 is a perspective view of a portable apparatus for surface inspection and electrolytic polishing according to the present disclosure.
Figure 2:
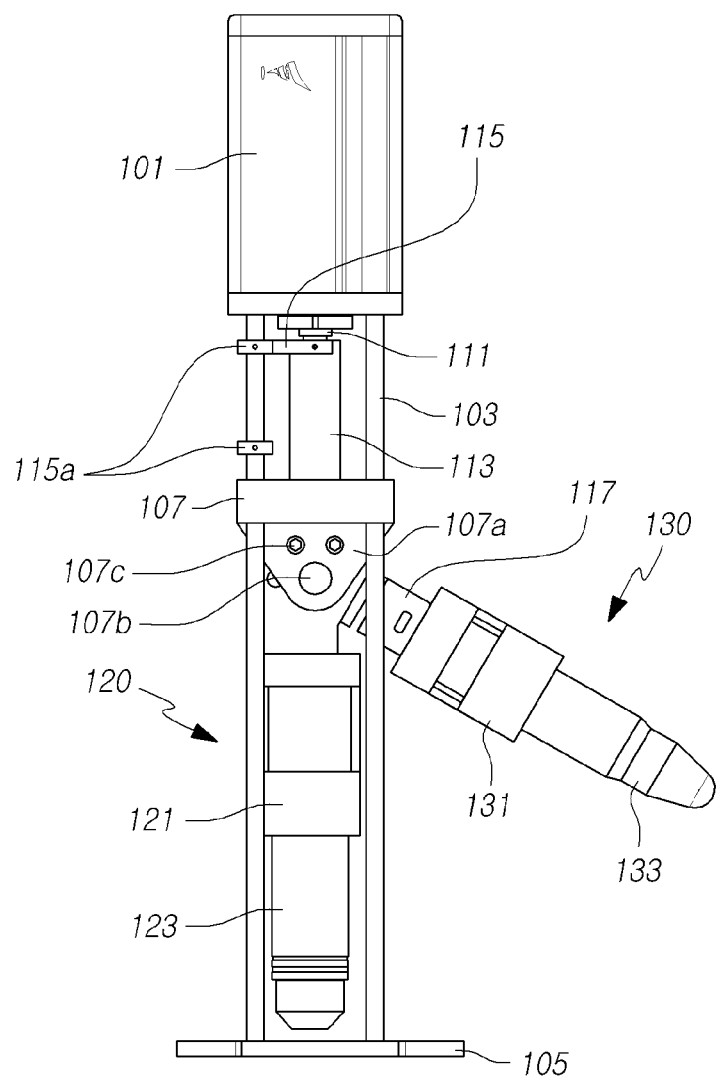
FIG. 2 is a front view of a portable apparatus for surface inspection and electrolytic polishing according to the present disclosure.
Figure 3:
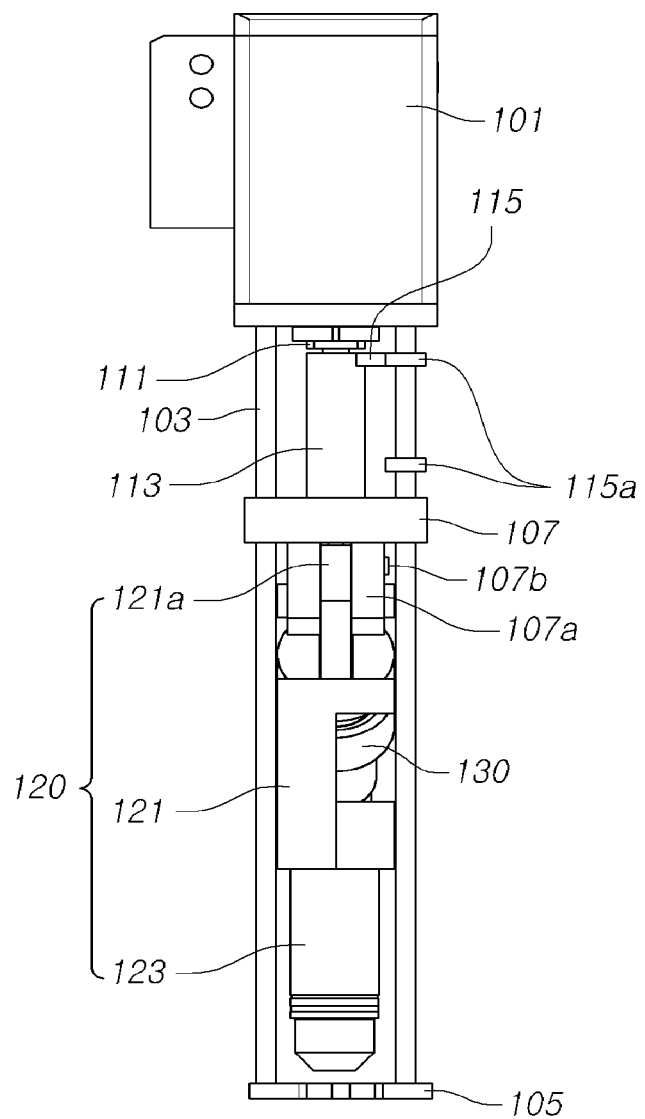
FIG. 3 is a side view of a portable apparatus for surface inspection and electrolytic polishing according to the present disclosure.

Hereinafter, embodiments will be described in greater detail with reference to the accompanying drawings.

Embodiments are described herein with reference to cross-sectional illustrates that are schematic illustrations of embodiments (and intermediate structures). As such, variations from the shapes of the illustrations as a result of, for example, manufacturing techniques and/or tolerances are to be expected. Thus, embodiments should not be construed as limited to the particular shapes of regions illustrated herein but may include deviations in shapes that result, for example, from manufacturing. In the drawings, lengths and sizes of layers and regions may be exaggerated for clarity. Like reference numerals in the drawings denote like elements.

Terms such as 'first', 'second', 'A', 'B', '(a)', '(b)' and the like may be used to describe various components, but they should not limit the various components. Those terms are only used for the purpose of differentiating a component from other components. For example, a first component may be referred to as a second component, and a second component may be referred to as a first component and so forth without departing from the spirit and scope of the present invention. Furthermore, 'and/or' may include any one of or a combination of the components mentioned. Furthermore, 'connected/accessed/coupled' represents that one component is directly connected, accessed, or coupled to another component or indirectly connected, accessed, or coupled through another component.

Although exemplary embodiments can be described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

As illustrated in FIGS. 1-5, a portable apparatus for surface inspection and electrolytic polishing according to an embodiment of the present disclosure can include a housing 101 where a motor and controller are embedded, a screw axis 109 that may be rotated by the motor, a cylinder 113 that accommodates a ball nut 111 coupled to the screw axis 109 and that is coupled to a slider 107 that will be explained hereinafter, and a plurality of guide members 103 each having an upper end coupled to the housing 101 and a lower end coupled to a base plate 105 and therefore fixed thereto.

The apparatus can also include the slider 107 through which the guide members 103 penetrate and therefore are coupled and that moves up and down together with the cylinder 113 along the guide members 103 during operation, and a surface inspector 120 and electrolytic polisher 130 that are coupled to the slider 107 and therefore move up and down together with the slider 107.

The portable apparatus for surface inspection and electrolytic polishing can include the surface inspector 120, the electrolytic polisher 130, and a frame that supports and moves the surface inspector 120 and the electrolytic polisher 130 up and down. The surface inspector 120 and the electrolytic polisher 130 can rotate to change positions and move up and down. The surface inspector 120 and the electrolytic polisher 130 are supported by the frame and rotated, and can be moved up and down by the motor. The frame can include the housing 101, screw axis 109, ball nut 111, cylinder 113, guide member 103, slider 107, and base plate 105.

A motor for driving the screw axis 109 can be embedded in the housing 101. A controller including a switch for operating the motor can also be embedded in the housing along with a circuit and switch for controlling the up/down movement of the surface inspector 120 and the electrolytic polisher 130 by means of a limit sensor 115 at an upper end of the frame. A plurality of guide members 103 formed in pillar shapes can be coupled to a lower end of the housing 101. The guide members 103 can be coupled in parallel to an exterior portion of the housing 101 such that the screw axis 109 is positioned in a central portion of the guide members 103.

Figure 4:
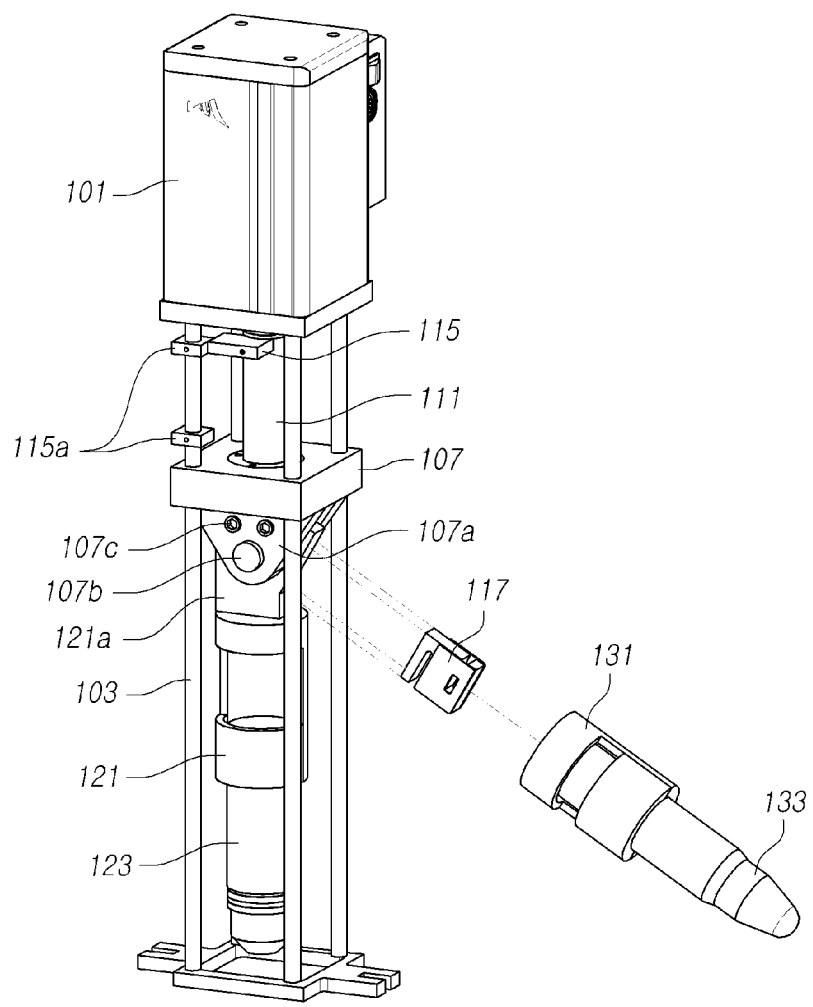
FIG. 4 is a perspective view of a portable apparatus for surface inspection and electrolytic polishing according to the present disclosure.
Figure 5:
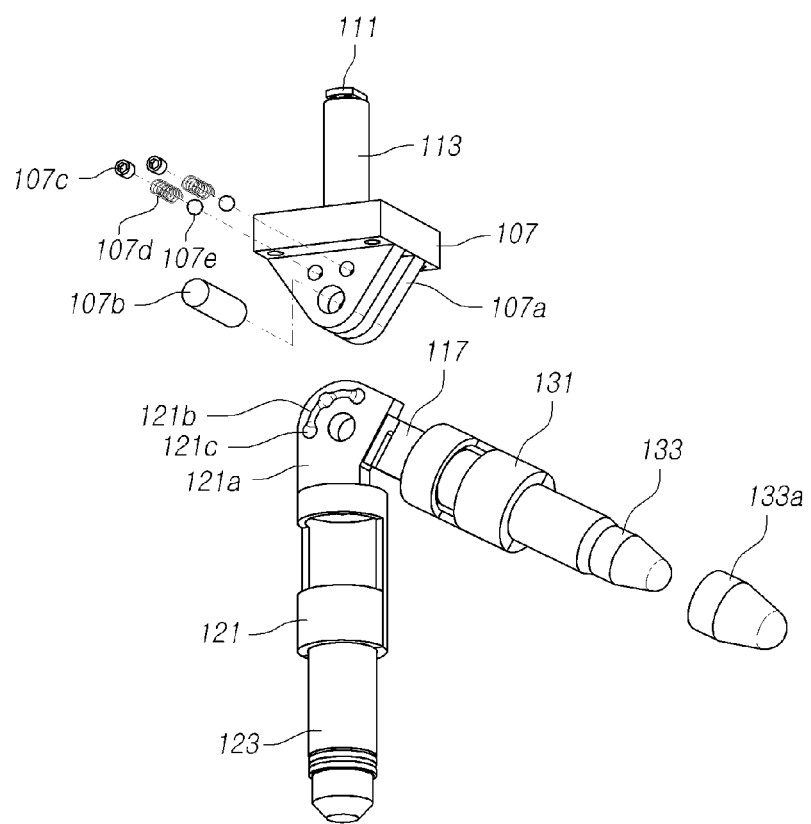
FIG. 5 is an exploded perspective view of a part of a portable apparatus for surface inspection and electrolytic polishing according to the present disclosure.

In FIGS. 1 and 4, four guide members 103 are illustrated as an example, but there is no limitation thereto. At least three guide members 103 can be arranged perpendicularly on the lower end of the housing 101. The guide members 103 can be distanced from one another as much as needed such that the screw axis 109, cylinder 113, surface inspector 120, and the electrolytic polisher 130 can be arranged between the guide members 103. Furthermore, at an opposite end of the guide members 103, a base plate 105 with a hole in the middle can be coupled to rigidly support the guide members 103, and the slider 107 that moves the surface inspector 120 and the electrolytic polisher 130 up and down can be coupled between both ends of the guide members 103.

The screw axis 109 can be arranged downwards from the center of the housing 101 and can be configured to be rotated by the motor. The screw axis 109 can also be configured to be coupled to the ball nut 111 and therefore to change a rotating motion into a straight line motion. The ball nut 111 can be coupled to the cylinder coupled to the slider 107. Therefore, when the motor is driven and the screw axis 109 rotates, the ball nut 111 can move up and down along the screw axis 109. The cylinder 113 and the slider 107 to which the ball nut 111 is coupled can move along the screw axis 109, as well. Because the guide members 103 penetrate the slider 107, the slider 107 can be guided and supported by the guide members 103 when moving up and down.

Furthermore, the limit sensor 115 can be coupled at an upper end of the cylinder 113, and a pair of position members 115a can be arranged on a guide member 103 positioned at an upper side of the slider 107. The pair of position members 115a can be configured for setting up/down movement positions of the limit sensor 115. The pair of position members 115a can also be arranged distanced from each other in an up and down direction such that they can control the up and down positions of the surface inspector 120 and the electrolytic polisher 130, thereby preventing damage or deformation thereof. The surface inspector 120 can be configured to inspect the surface structure state of a test subject, in other words, to photograph the etched surface illumination state of the test subject, the fine circuitry state of an IC chip, the foreign substance attachment state of a semiconductor surface, and the like with an imaging device such as a micro digital camera, and to transmit the photographed result. In the present disclosure, the surface inspector 120 can be mainly used to make an image of an electrolyzed polished metal surface of the test subject right before an indentation test.

The surface inspector 120 can be provided with an inspection head 123 to which an imaging device such as a digital camera is embedded, and a head housing 121 to which the inspection head 123 can be coupled and which can be coupled in turn to the slider 107. A highlight LED for lighting during a photographing operation of the micro digital camera can be embedded in the inspection head 123. The head housing 121 can be formed in a pipe shape, of which one side is cut. The inspection head 123 can be inserted into the one side of the head housing 121 and coupled thereto. The other side of the head housing 121 can be coupled to the slider 107 and thereby supported, and a wire of the inspection head 123 can be exposed through the cut portion.

The slider 107 can be formed in a flat square block shape of which a lower end can have a pair of hub plates 107a that extend from a lower side of the slider 107 and that can be distanced from one another so that the head housing 121 can be inserted and coupled thereto. Furthermore, at an end of the head housing 121, an extension flange 121a can be provided that is configured to be inserted between the hub plates 107a that are distanced from one another and to be hinge-coupled, so that the head housing 121 can make a rotating motion with the head housing 121 coupled to the slider 107.

On the extension flange 121a of the head housing 121, a hinge hole can be formed that communicates with the hub plate 107a of the slider 107 so that the head housing 121 can be coupled to the hub plate 107a by a hinge axis 107b. With the electrolytic polisher 130 that will be explained hereinafter coupled to an end of the extension flange 121a, the surface inspector 120 and the electrolytic polisher 130 can rotate around the hinge axis 107b, and therefore a user can select and use one of the surface inspector 120 and/or the electrolytic polisher 130 as necessary.

Such an extension flange 121a can be provided with a hinge hole, and a guide groove 121b of a circular shape distanced from the hinge hole and having the hinge hole as a center, i.e. at a center point of the circular shape. The hub plate 107a can be provided with a pair of penetration holes distanced from one another and arranged in a corresponding position to the guide groove 121b of the extension flange 121a such that the penetration holes align with the guide groove 121b. Furthermore, a ball 107e that is configured to make a roll-motion along the guide groove 121b of the extension flange 121a and an elastic body 107d that elastically supports the ball 107e can be inserted into either of the penetration holes of the hub plate 107a. A securing member 107c can be formed in each of the penetration holes of the hub plate 107a to be screw-fastened to the penetration hole while supporting the elastic body 107d.

At both ends of the guide groove 121b, a resting groove 121c can be formed to have a deeper depth than the guide groove 121b, so that once the ball 107e making a roll-motion along the guide groove 121b rests in the resting groove 121c, the ball 107e no longer makes a movement beyond the guide groove 121b. Therefore, when selecting one of the surface inspector 120 and the electrolytic polisher 130 for operation, the user may rotate the head housing 121 with his/her hand, and then the ball 107e that used to be elastically supported by the elastic body 107d and therefore rested in the resting groove 121c can move along the guide groove 121b as the ball 107e compresses the elastic body 107d. When the movement is completed and the ball 107e is inserted into the resting groove 121c at an opposite side as a starting side, the elastic body 107d can expand again and support the ball 107e. Positions of the surface inspector 120 and electrolytic polisher 130 can be set by completing a motion of the ball 107e.

When the ball 107e is resting in both resting grooves 121c of the guide groove 121b, the ball 107e will not deviate away from the guide groove 121b because of the supporting force of the elastic body 107d and instead will be fixed. The positions of the ball 107e inserted into each of the resting grooves 121c can therefore become the setting positions of the surface inspector 120 and the electrolytic polisher 130. In these positions, the central axes of the surface inspector 120 and the electrolytic polisher 130 will be parallel to the guide member 103. Furthermore, in the guide groove 121b, another resting groove 121c can be formed in a middle point between the two resting grooves 121c of the guide groove 121b, that is, at a midpoint of the guide groove 121b, so that the ball 107e may rest in the resting groove 121c in both positions where the surface inspector 120 is parallel to the guide member 130 and where the electrolytic polisher 130 is parallel to the guide member 103.

Meanwhile, the electrolytic polisher 130 is an apparatus configured to electrolyze a surface of a processing subject to polish the surface by applying a voltage between an anode and a cathode, having the processing subject made of a metal that can be dissolved in an electrolytic solution as the anode and having the processing metal that cannot be dissolved in the electrolytic solution as the cathode. The electrolytic polisher 130 can be provided with a probe 133 in which an electrode is embedded and a probe housing 131 to which the probe 133 can be coupled and which can be coupled to the slider 107. A load cell 117 that is configured to measure a load being applied to the test subject by the probe 133 can be mounted at an end of the probe housing 131, and thus the end of the extension flange 121a can be coupled to the load cell 117.

In the electrolytic polisher 130, a probe tip 133a that is configured to absorb an electrolyte solution and to allow current to flow between the test subject and the probe 133 can be coupled to an end of the probe 133. The probe tip 133a can be made of fabric so that the electrolyte solution can be absorbed quickly, and one side covering the end of the probe 133 can be formed in a closed thimble shape. As explained above, it is possible to test a surface inspector and an electrolytic polisher on a test subject in a variety of industrial fields, such as machinery, construction, chemicals, and the like, regardless of the testing place, thereby reducing cost and a required process.

Furthermore, there is an effect of reducing required manpower and time for installing a surface inspector and an electrolytic polisher. In the aforementioned descriptions, all of the components of the present disclosure described as being coupled to one another and operating with one another should not be construed for the purpose of limitation. That is, one or more of the components may be selectively coupled and operated in a variety of ways as long as they are within the scope of the purpose of the present disclosure.

Furthermore, terms such as "include", "form", and "have" mean that corresponding components can be included but do not exclude other components not mentioned. Other components may be included.

Furthermore, in the aforementioned, a singular form may include a plural form as long as it is not specifically mentioned in a sentence. Furthermore, 'include/comprise' or 'including/comprising' used in the specification represents that one or more components, steps, operations, and elements exist or are added. Furthermore, unless defined otherwise, all the terms used in this specification including technical and scientific terms have the same meanings as would be generally understood by those skilled in the related art. The terms defined in generally used dictionaries should be construed as having the same meanings as would be construed in the context of the related art, and unless clearly defined otherwise in this specification, should not be construed as having idealistic or overly formal meanings.

In the drawings and specification, typical exemplary embodiments of the invention have been disclosed, and although specific terms are employed, they are used in a generic and descriptive sense only and not for purposes of limitation. As for the scope of the invention, it is to be set forth in the following claims. Therefore, it will be understood by those of ordinary skill in the art that various changes in form and details may be made therein without departing from the spirit and scope of the present invention as defined by the following claims.

REFERENCE NUMERALS

101: HOUSING
103: GUIDE MEMBER
105: BASE PLATE
107: SLIDER
107a: HUB PLATE
109: SCREW AXIS
111: BALL NUT
113: CYLINDER
115: LIMIT SENSOR
117: LOAD CELL
120: SURFACE INSPECTOR
121: HEAD HOUSING
121a: EXTENSION FLANGE
121b: GUIDE GROOVE
121c: RESTING GROOVE
123: INSPECTION HEAD
130: ELECTROLYTE POLISHER
131: PROBE HOUSING
133: PROBE
133a: PROBE TIP

What is claimed is:

1. A portable apparatus for surface inspection and electrolytic polishing, the apparatus comprising:
a housing having a motor and controller embedded therein;
a screw axis configured to be rotated by the motor;
a cylinder configured to accommodate a ball nut coupled to the screw axis, and configured to be coupled to a slider;
a plurality of guide members, each of which having an upper end coupled to the housing and a lower end coupled to a base plate;
the slider through which the guide members penetrate and couple thereto, the slider being configured to move up and down along the guide members together with the cylinder during operation of the motor; and
a surface inspector and an electrolytic polisher coupled to the slider and configured to move up and down together with the slider, the surface inspector being provided with an inspection head having a digital camera embedded therein, and a head housing being provided to which the inspection head is coupled and which is coupled to the slider,
wherein the slider is provided with a pair of hub plates that are distanced from one another and that extend from a lower side of the slider, and an end of the head housing is provided with an extension flange that is inserted between the hub plates and is hinge-coupled.

2. The apparatus according to claim 1,
wherein a limit sensor is coupled to an upper end of the cylinder, and a position member configured to set an up/down movement position of the limit sensor is coupled to the guide members.

3. The apparatus according to claim 1,
wherein the extension flange is provided with a hinge hole that communicates with the hub plates so as to be coupled to the hub plates by a hinge axis.

4. The apparatus according to claim 3, wherein
the extension flange is provided with a guide groove of a circular shape distanced from the hinge hole and having the hinge hole at a center of the circular shape;
the hub plates are each provided with a pair of penetration holes distanced from one another and aligned with the guide groove;
a ball configured to make a roll-motion along the guide groove and an elastic body configured to elastically support the ball are configured to be inserted into the penetration holes, and a fastening member is configured to be screw-fastened with each of the penetration holes while supporting the elastic body.

5. The apparatus according to claim 4,
wherein at both ends of the guide groove, a resting groove is formed having a deeper depth than the guide groove, and where the ball rests.

6. The apparatus according to claim 1,
wherein the electrolytic polisher includes a probe with an electrode embedded therein and a probe housing to which the probe is coupled and which is coupled to the slider.

7. The apparatus according to claim 6,
wherein a load cell is mounted at one end of the probe housing and is configured to measure a load being applied to a test subject by the probe, and the load cell and an end of the extension flange are coupled to each other.

8. The apparatus according to claim 7,
wherein the electrolytic polisher has a probe tip (i) coupled to an end of the probe, (ii) configured to absorb an electrolyte solution, and (iii) configured to allow current to flow between the test subject and the probe.

9. A portable apparatus for surface inspection and electrolytic polishing comprising:
a housing;
a plurality of guide members, each guide member having an upper end coupled to the housing and a lower end coupled to a base plate;
a slider coupled to the guide members and configured to slidably move along the guide members, the slider having a pair of hub plates distanced from one another and extending from a lower side of the slide;
a surface inspector having an imaging device and an electrolytic polisher coupled to one another and coupled to the slider, and an extension flange being coupled to the surface inspector and the imaging device, the extension flange having a guide groove, wherein the hub plates are provided with a pair of penetration holes distanced from one another and aligned with the guide groove, and a ball configured to roll along the guide groove and an elastic body configured to elastically support the ball are configured to be inserted into the penetration holes.

10. The apparatus according to claim 9, wherein the surface inspector and the imaging device are hinge-coupled to the slider.

11. The apparatus according to claim 9, wherein a resting groove is formed at each end of the guide groove having a deeper depth than the guide groove and being configured to allow the ball to rest therein.

12. The apparatus according to claim 11, wherein a middle resting groove is formed at a midpoint of the guide groove having a deeper depth than the guide groove and being configured to allow the ball to rest therein.

\* \* \* \* \*